US008792961B2

United States Patent
Gross et al.

(10) Patent No.: US 8,792,961 B2
(45) Date of Patent: Jul. 29, 2014

(54) METHOD FOR OBTAINING MAGNETIC RESONANCE IMAGE DATA USING A MULTI-ECHO MR SEQUENCE WITH IMPROVED SIGNAL-TO-NOISE RATIO OF THE PHASE INFORMATION

(75) Inventors: Patric Gross, Langensendelbach (DE); Joerg Roland, Hemhofen (DE)

(73) Assignee: Siemens Aktiengesellschaft, Munich (DE)

( * ) Notice: Subject to any disclaimer, the term of this patent is extended or adjusted under 35 U.S.C. 154(b) by 811 days.

(21) Appl. No.: 12/901,679

(22) Filed: Oct. 11, 2010

(65) Prior Publication Data

US 2011/0092801 A1    Apr. 21, 2011

(30) Foreign Application Priority Data

Oct. 15, 2009   (DE) .................. 10 2009 049 520

(51) Int. Cl.
    *A61B 5/05*         (2006.01)
(52) U.S. Cl.
    USPC ........................... 600/412; 600/410; 324/315
(58) Field of Classification Search
    USPC .......... 600/407, 410, 412, 437; 324/307, 309, 324/312, 313, 315
    See application file for complete search history.

(56) References Cited

U.S. PATENT DOCUMENTS

| 4,833,407 | A  | * | 5/1989  | Holland et al. | ............... | 324/309 |
|-----------|----|----|---------|----------------|------|---------|
| 5,798,642 | A  | * | 8/1998  | Watanabe       | ............... | 324/307 |
| 8,143,889 | B2 | * | 3/2012  | Jeong et al.   | .................. | 324/309 |
| 2004/0010191 | A1 | * | 1/2004 | Yatsui      | ........................ | 600/410 |
| 2004/0135577 | A1 | * | 7/2004 | Yatsui et al. | ................. | 324/307 |
| 2006/0064002 | A1 | * | 3/2006 | Grist et al. | .................... | 600/410 |
| 2006/0241389 | A1 | * | 10/2006 | Assmann et al. | ............ | 600/419 |
| 2008/0054900 | A1 | * | 3/2008 | Polzin       | ........................ | 324/309 |
| 2009/0096450 | A1 | * | 4/2009 | Roland      | ........................ | 324/315 |
| 2009/0256567 | A1 | * | 10/2009 | Aksit et al. | .................. | 324/312 |

* cited by examiner

*Primary Examiner* — Unsu Jung
*Assistant Examiner* — Michael N Fisher
(74) *Attorney, Agent, or Firm* — Schiff Hardin LLP

(57) ABSTRACT

In a method and magnetic resonance (MR) system to create an MR magnitude image data set and a phase image data set of an examination subject, first echo signals in a first raw MR data set are detected after a first echo time TE1 and at least second echo signals in at least one second raw MR data set are detected after a second echo time TE2 that is longer than TE1, a magnitude image data set is generated on the basis of the first raw MR data set and the at least one second raw MR data set with averaging of the first and the at least one second raw MR data set, and the phase image data set is generated based on the phase information contained in the at least two raw MR data sets, with averaging of the respective phase information contained in the at least two raw MR data sets.

8 Claims, 2 Drawing Sheets

METHOD FOR OBTAINING MAGNETIC RESONANCE IMAGE DATA USING A MULTI-ECHO MR SEQUENCE WITH IMPROVED SIGNAL-TO-NOISE RATIO OF THE PHASE INFORMATION

BACKGROUND OF THE INVENTION

1. Field of the Invention

The invention concerns: a method to create a magnetic resonance (MR) magnitude image data set and a phase image data set of an examination subject; an MR system and a computer-readable data storage medium for implementing such a method in a computerized processor.

2. Description of the Prior Art

One application field of magnetic resonance systems is the monitoring of medical procedures or treatments, for example thermotherapy, in which the temperature in tissue (for example tumor cells) is specifically increased, which ideally leads to cell death or (given a smaller temperature increase) allows the cells to become more sensitive to accompanying therapy measures such as chemotherapy or radiation therapy. A cooling is likewise possible in a treatment known as cryotherapy. Particularly in the case of ablation of tumor tissue (for example by means if high-intensity focused ultrasound), magnetic resonance systems are increasingly commonly used for 3-dimensional temperature imaging in order to show the temperatures prevailing in the treated area with optimally high precision and high time resolution during a treatment. Optical monitoring during the treatment should not only show the temperature of the heated tissue with time and spatial resolution, but also it should be possible to establish a relationship of the measured temperature images with the anatomy of the examined person.

One possibility to show temperature changes with the use of magnetic resonance tomography is the proton resonance frequency method that is based on the temperature dependency of the resonant frequency of protons. The phase information of the MR signal that is obtained from gradient echo signals is used in order to conclude a temperature change from the difference of two phase images. The temperature information can be shown with spatial resolution through the presentation of phase difference images. The relation between phase change and a temperature changes is as follows:

$$\phi=\gamma B_0 TE\alpha T, \text{ or } \Delta\phi=\gamma B_0 TE\alpha T, \quad (1)$$

wherein $B_0$ is the basic magnetic field strength, $\gamma$ is the gyromagnetic ratio, TE is the echo time, $\alpha$ is the temperature dependency of the resonance frequency (which is −0.01 ppm/° C.) and $\Delta T$ is the temperature change. Since the acquired MR data that are used to create the phase differences are plagued with noise, the temperature changes determined from them can be determined only with a limited precision. As can be recognized from the above equation, it would be advantageous to select the echo time to be as long as possible in order to induce an optimally large phase change; however, this extends the acquisition time and reduces the signal-to-noise ratio overall since the signal level overall decreases with increasing echo time due to the T2* decay of the magnetization.

SUMMARY OF THE INVENTION

An object of the present invention is to provide a method in which phase information in an MR phase image can be determined with improved precision.

According to a first aspect of the invention, a method is provided to generate an MR magnitude image data set and a phase image data set of an examination subject, wherein first echo signals are acquired in a first raw data set after a first echo time TE and at least second echo signals are acquired in a second raw MR data set after a second echo time TE2 that is longer than TE1. The magnitude image data set can subsequently be determined on the basis of the first raw MR data set and the at least one second raw MR data set with averaging of the first and the at least one second raw MR data set. Furthermore, the phase image data set is generated with the use of the phase information contained in the at least two raw MR data sets, and the respective phase information contained in the at least two raw MR data sets is averaged. Overall the signal-to-noise ratio in the phase information can be increased by the use of the phase information at the different echo times, which reduces errors in the phase information overall.

The phase information in the phase image data set contains typical information about a physical variable that is connected with the phase information through a formula. According to one embodiment of the invention, in the averaging of the phase information the averaging is implemented depending on a connection of the phase information with the physical variable in the formula. Since the phase images are typically not used as such in most applications (rather the phase information allows a conclusion of data such as temperature, flow or the like), a noise of the phase images for different echo times can indicate a varying strength of the signal-to-noise ratio of the corresponding physical variable. In this case a simple arithmetic averaging is no longer productive and a weighting must be conducted corresponding to the physical formula that underlies the specific phase information. This is explained in the following example. If an identical phase noise is assumed at the different echo times—for example a specific value of 2°—according to the above Equation (1) this means a smaller error given a large echo time than given a shorter echo time. Assuming that, for example, a phase difference of $\Delta\phi=11°$ corresponds to a temperature difference of $\Delta T=1°$ C. given TE=50 ms, the phase change per ° C. is only half as large (i.e. 5°) given a TE of approximately 25 ms. If a phase noise of 2° is assumed for both measurements, it is apparent that the 2° mean a larger error given the shorter time than given the longer echo time. By taking into account the formula which specifies the connection between phase information and physical variable, the correct averaging of the different phase information at the different echo times can result.

In the generation of the phase image data set, the averaging of the phase information contained in the at least two raw data sets ensues depending on noise of the respective phase information contained in the raw data set. The averaging in particular ensues depending on the variance of the respective phase information contained in the raw data set. Strictly speaking, this applies only for a noise with Gaussian distribution, which is not necessarily the case in every image data set. It is, however, a good approximation.

If this method to determine the phase information is applied to temperature imaging, the temperature difference is determined from the difference of two phase image data sets using a variance, under consideration of the averaging of the individual items of phase information depending on the connection between phase information and temperature difference. The spatially resolved temperature change is advantageously calculated as follows in a pixel image point i,j:

$$\Delta T_{ij} = \frac{1}{\sum_{n=1}^{N} TE_n} \left( \sum_{n=1}^{N} TE_n \Delta T_{ij}^n \right) = \frac{k}{\sum_{n=1}^{N} TE_n} \left( \sum_{n=1}^{N} \Delta \varphi_{ij}^n \right) \quad (2)$$

wherein $TE_n$ is the n-th echo of a multi-gradient echo sequence with at least N echoes per excitation pulse. For example, N can be between 3 and 5. $\Delta T_{ij}^n$ is the temperature difference, pixel i,j is calculated from the n-th echo and $\Delta \phi_{ij}^n$ is the associated phase difference.

One problem in the determination of a physical variable based on a phase value can be that, after a phase transition given the limit of $2\pi$, the result value can no longer be unambiguously associated. A specific phase value or, respectively, a specific phase difference $\phi_0$ can correspond to $\phi = \phi_0 + N \cdot 2\pi$. The corresponding physical variable can no longer be unambiguously calculated with the equation. With regard to the temperature imaging this means that the temperature change $\Delta T$ can no longer be unambiguously determined. The phase information that is generated at the short first echo time can now be used. A value range of the phase information at other, greater echo times can be concluded from the value range of the phase values that are generated in the difference images at the first echo time, wherein it can be determined whether the additional value ranges exceed the value range of $2\pi$ and how often they exceed this value range of $2\pi$. For example, if the value range of the phase values at a first echo time comprises the phase values from zero to 200°, the value range at the doubled echo time already comprises 400°, wherein this 400° is represented in the value range between zero and 360° and a phase transition consequently occurs. Starting from the value range at the short echo time, the value ranges at the longer echo times can now be determined and the phase transitions can be corrected and accounted for in that the number of phase transitions is calculated in order to correctly determine the underlying physical variable.

DESCRIPTION OF THE PREFERRED EMBODIMENTS

Figure 1:
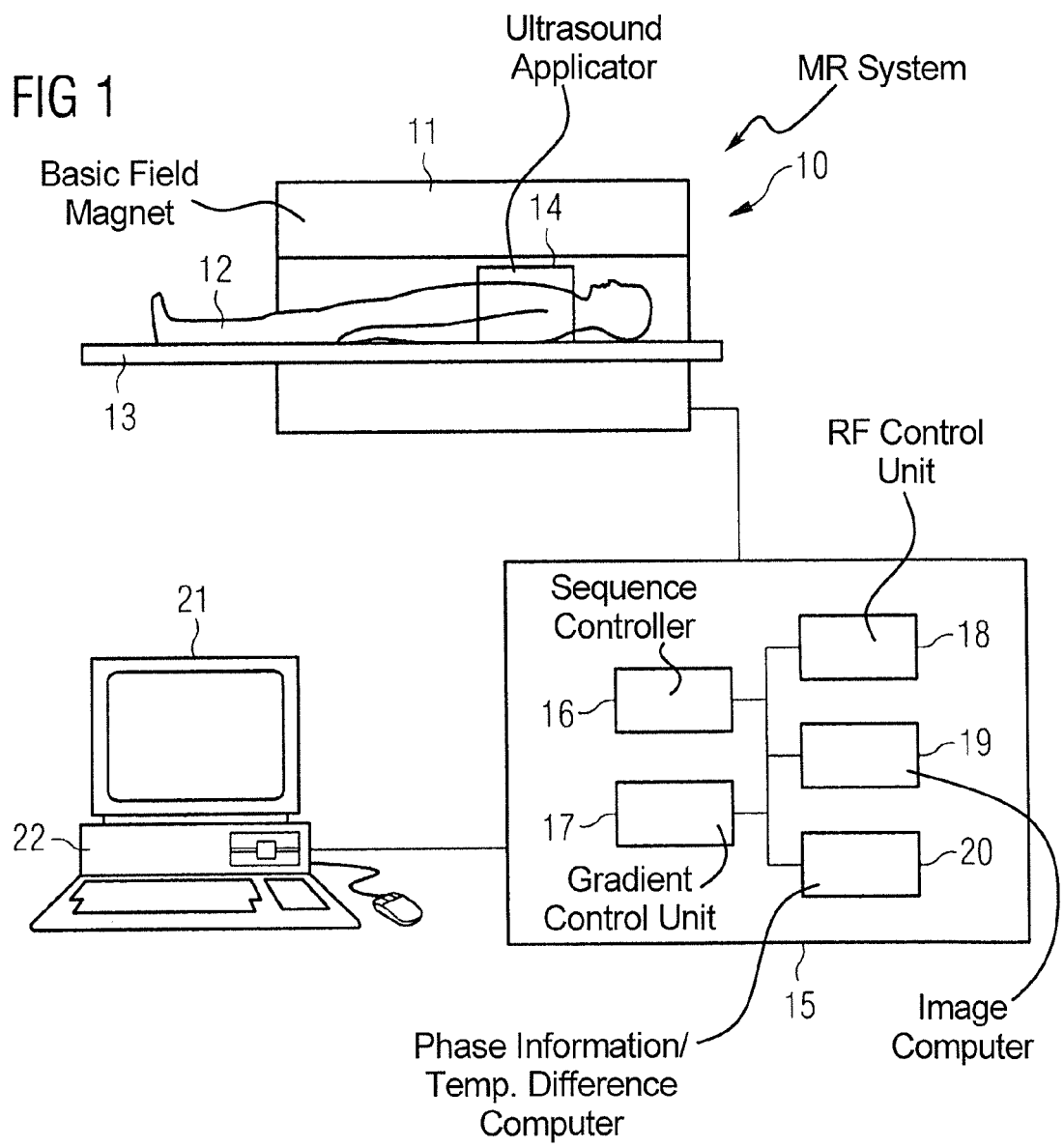
FIG. 1 schematically shows an MR system coupled with a therapy apparatus with which temperature information can be reliably determined.

An MR system 10 with a basic field magnet 11 to generate a $B_0$ field and to generate a resulting magnetization in an examined person 12 (who is arranged on a bed 13 in the MR system) is shown FIG. 1. Furthermore, a device for application of focused ultrasound—what is known as an ultrasound applicator 14—is shown with which the tissue of the examined person 12 can be specifically heated, for example to kill tumors. The MR system furthermore has a central control unit 15 with a sequence controller 16 in which the sequence of the radiated RF pulses and the magnetic field gradients is controlled. A gradient control unit 17 is provided to switch the gradients and an RF control unit 18 is provided to switch the RF pulses. An image computer 19 calculates an MR image from the MR signals detected with the aid of a coil (not shown), wherein the image computer can calculate a magnitude image or a phase image. How MR magnitudes or phase images can be generated via radiation of RF pulses and switching of gradients is familiar to those skilled in the art, such that a detailed description thereof is not necessary herein. Furthermore, a computer 20 can be provided that—as explained in the following—calculates phase information with improved signal-to-noise ratio and calculates a temperature difference from a phase difference, for example. It is likewise possible that the operations executed in the computer are implemented in the image computer 19. Furthermore, a display unit 21 and an input unit 22 are provided.

Figure 2:
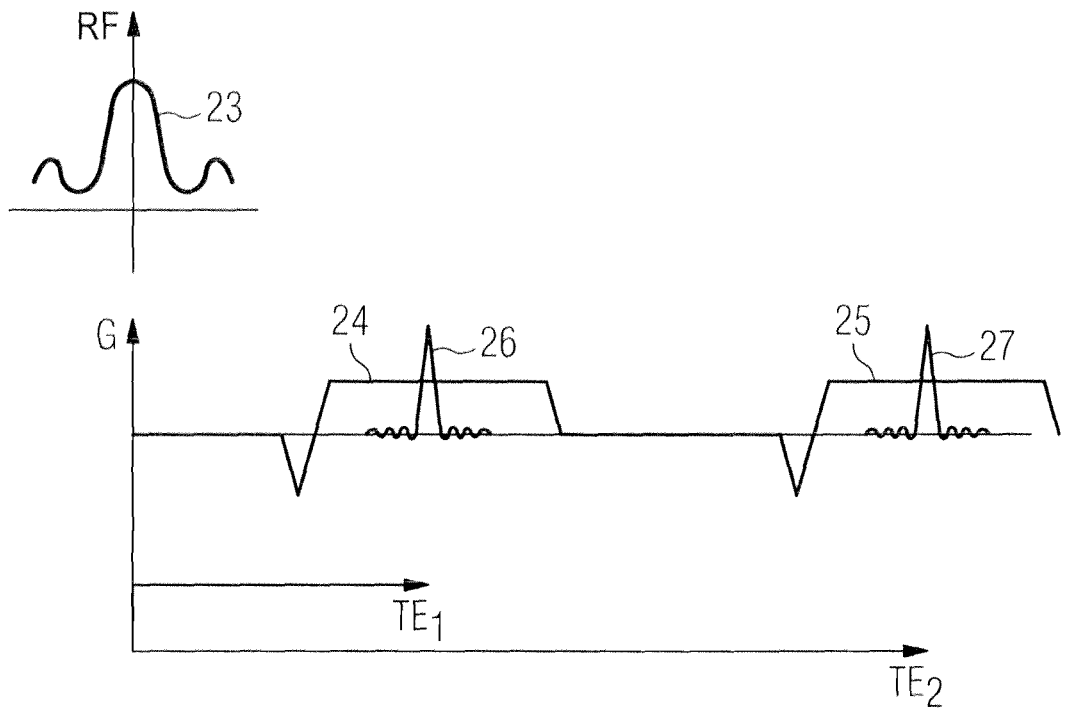
FIG. 2 shows a portion of a multi-echo sequence with generation of a first echo and a second echo.

A portion of a multi-echo gradient sequence with which temperature changes can be presented according to the invention (as described in the following) is shown in FIG. 2. After radiation of an RF pulse 23, multiple bipolar gradients 24 and 25 are switched in the readout direction, which gradients 24 and 25 respectively lead to a gradient echo 26 and 27. The first gradient echo 26 ensues at a first echo point in time $TE_1$; the second gradient echo ensues at a second echo point in time $TE_2$. In the depiction of FIG. 2, only two gradient echoes are shown; however, multiple echoes—for example three to five echoes—can also be read out after an RF excitation pulse. The echo times can lie between 5 and 45 ms, for example. Temperature changes can be non-invasively shown with these gradient echo sequences since the temperature dependency of the chemical shift of the water protons is used. The magnetic field environment that is altered by the temperature-dependent chemical shift results in a temperature-dependent resonance frequency that can be shown in a temperature-dependent phase information at the point in time of the echo. The use of a gradient echo sequence is advantageous since this is sensitive to slight local magnetic field differences. The examined tissue accumulates a frequency-dependent (i.e. temperature-dependent) phase $\phi$ at the point in time of the echo TE. If the tissue is heated and the measurement is repeated at a later point in time, a per-pixel temperature change can be concluded according to the above Equation (1) by taking the per-pixel difference in the phase images. As mentioned above, a linear connection between phase change and temperature change results according to the following relationships $$\Delta\phi \sim TE \cdot B_0 \cdot \Delta T \text{ or}$$

$$k \cdot \Delta\phi = TE \cdot \Delta T \quad (3)$$

The magnitude image generated with the aid of the imaging sequence from FIG. 2 has an improved signal-to-noise ratio since the MR signals acquired at different points in time TE can be averaged. A simple example of this is the arithmetic averaging of the magnitude images $M_n$ with $$M_{total} = \sum_{n=1}^{N} M_n \quad (4)$$

This leads to an improvement of the signal-to-noise ratio with a factor of $\sqrt{N}$. This generally known effect is utilized if multiple images are acquired in succession with identical acquisition parameters in the MR imaging and the images are then added. In addition to the magnitude images, it is also possible to improve the phase image quality. However, since phase images are typically not used as such (but rather offer conclusions about functional data such as temperature, flow or the like), noise of the phase images for different echo times can indicate a signal-to-noise ratio of varying strength for the corresponding physical variables. In this case a simple arithmetic averaging is no longer productive and a weighting must be conducted corresponding to the physical relationship that underlies the specific variable. Such averagings are generally designated as weighted averages and take place according to the formula $$\overline{m} = \frac{1}{\sum_{n=1}^{N} W_n} \left( \sum_{n=1}^{N} W_n m_n \right) \quad (5)$$

wherein $\overline{m}$ is the averaged variable and $W_n$ are the weighting factors for the N components $m_n$ over that are averaged. According to the invention, it is now possible to use the connection between physical variable and phase information in the averaging of the phase images in order to implement the averaging.

The optimal weighting in the averaging depends on the noise or, respectively, the underlying statistical distribution of the measurement variable over which it should be averaged. The averaging is frequently conducted in a form in which the noise of the different components is normalized. An optimal weighting of measurement variables whose noise has a Gaussian distribution is an averaging with regard to the variances $V_n$ of the individual components.

For $$w_n = \frac{1}{V_n},$$

the following Equation results from the above Equation:

$$\overline{m} = \frac{1}{\sum_{n=1}^{N} \frac{1}{V_n}} \left( \sum_{n=1}^{N} \frac{1}{V_n} m_n \right) \quad (6)$$

It can be formally shown that a distribution with identical average value and minimal variance is created with this averaging. Since phase images only have a Gaussian distribution in the boundary case of a very low phase noise, other weighted averagings can also be necessary for an optimal phase image precision. Above Equations (1) through (3) describe the connection between phase change and temperature change. If the phase image data sets that are subtracted from one another are now acquired with larger, different echoes, and if an identical phase noise in all spatially resolved phase images $\phi_{ij}^n$ at the pixel position i,j is assumed, a suitably weighted averaging ensues as follows under consideration of the above Equations:

$$\Delta T_{ij} = \frac{1}{\sum_{n=1}^{N} TE_n} \left( \sum_{n=1}^{N} TE_n \Delta T_{ij}^n \right) = \frac{k}{\sum_{n=1}^{N} TE_n} \left( \sum_{n=1}^{N} \Delta \phi_{ij}^n \right) \quad (7)$$

wherein $\Delta T_{ij}$ the averaged, spatially resolved temperature at the pixel i,j, $\Delta T_{ij}^n$ corresponds to the spatially resolved temperature determined from the phase difference images of the respective echo n with the associated echo point in time $TE_n$, and $\Delta \phi_{ij}^n$ is the associated phase difference.

With the relationship for the variances for temperature $V_n^T$ and phase $V_n^\Phi$ of $\Delta T$ and $\Delta \phi$ using the above Equation (3), it then applies that $$V_n^T = \frac{k^2}{TE_n^2} V_n^\varphi \quad (8)$$

and the following results with the above Equation (7):

$$\Delta T_{ij} = \frac{1}{\sum_{n=1}^{N} (TE_n)^2} \left( \sum_{n=1}^{N} (TE_n)^2 \Delta T_{ij}^n \right) = \frac{k}{\sum_{n=1}^{N} (TE_n)^2} \left( \sum_{n=1}^{N} \Delta TE_n \varphi_{ij}^n \right) \quad (9)$$

As is apparent from Equation (9), the temperature difference can be determined with the aid of the individual echo times and the phase differences belonging to the individual echo times.

If the resolution or bandwidth should be varied in addition to the echo sequence imaging parameters, corresponding weightings for these variables must likewise be taken into account.

Figure 3:
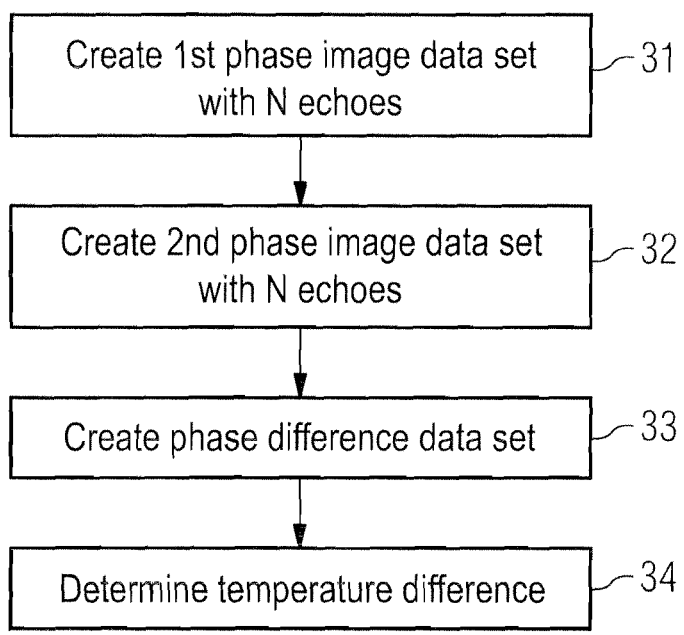
FIG. 3 is a flow diagram with the steps that are necessary to reliably determine the temperature difference.

The steps with which the temperature difference can be calculated as mentioned above are now summarized in FIG. 3. After creating a first phase image data set with N echoes in Step 31 and the creation of an additional phase image data set at a later point in time in Step 32 (for example during the heating of the tissue), the two phase image data sets can be subtracted from one another to generate a phase difference image data set in Step 33. The temperature difference in the individual pixels can be determined in Step 34 via the above Equation (9). In the determination of the temperature difference the problem can now occur that this can no longer by unambiguously established since only phase values between zero and 2π are shown, and in taking the difference it cannot be absolutely established whether a phase transition was present or not. Typical echo times TE in a basic magnetic field of 1.5 Tesla cover a range from 70 to 200° C., which is sufficient for the temperature difference depiction. However, for higher fields of 3 Tesla this range of non-ambiguity of the temperature calculation is already halved to 35 to 50° C. Add to this that in many cases the optimal echo times TE for the MR temperature imaging are markedly higher than at 1.5 Tesla. The removal of the phase transition in the phase information is thus necessary. This applies all the more for the temperature imaging at 7 Tesla. Since the importance of 7 Tesla is significantly increasing in MR apparatuses, the removal of the phase transition for the MR temperature imaging is important since here only an unambiguous phase value range over a temperature range of 10 to 15° C. can be achieved. According to the invention, this is now possible with the use of the value ranges at the short echo times. For example, a phase difference image can only be generated with the aid of the phase information that is acquired at the echo point in time $TE_1$. Given a heating this shortest echo point in time leads to a predetermined value range at phase differences, for example a value range from 0° to 150°. If the echo time is doubled, given the same temperature change the value range is already at 300°; if even longer echo times are used the value range is thus no longer situated within 2π. With the aid of the value range at the short echo time it can now be determined how many phase transitions must be present at the longer echo points in time since a linear connection between echo time and phase change (and therefore between echo time and phase value range) exists.

The calculation of phase information from the multiple echoes N is typically necessary without movement correction since the movement of the examined subject that occurs within the different echo times can normally be ignored.

Although modifications and changes may be suggested by those skilled in the art, it is the intention of the inventor to embody within the patent warranted hereon all changes and modifications as reasonably and properly come within the scope of his contribution to the art.

We claim as our invention:

1. Method to display a representation of a temperature in a magnetic resonance (MR) image of an examination subject, comprising the steps of:
    operating an MR data acquisition unit according to an MR data acquisition pulse sequence, while the examination subject is situated in a basic magnetic field $B_0$ in the data acquisition unit, wherein nuclei in the examination subject are excited at a resonance frequency and first echo signals from the excited nuclei are detected after a first echo time TE1 in said sequence and second echo signals from the excited nuclei are detected after a second echo time TE2 in said sequence that is longer than TE1;
    in a processor, generating a first raw MR data set in which said first echo signals are represented and generating at least one second raw MR data set in which said second echo signals are represented, thereby producing at least two raw MR data sets, each of said at least two raw MR data sets comprising magnitude information, and phase information $\phi$, and said phase information $\phi$ in each of said at least two raw MR data sets having a relation to temperature T of the examination subject that is dependent on the respective echo time during which the respective echo signals were acquired that are represented in the at least two raw MR data sets, according to $\phi=\gamma B_0 TE\alpha T$, wherein $\phi$ is $\phi_1$ or $\phi_2$, $\gamma$ is the gyromagnetic ration for said nuclei, TE is TE1 or TE2, and $\alpha$ is the dependency of T on the resonance frequency of the nuclei;
    in a processor, generating a magnitude image data set from the at least two raw MR data sets by averaging the magnitude information in the at least two raw MR data sets;
    in said processor, generating a phase image data set from the phase information $\phi$ contained in the at least two raw MR data sets, by weighting respective phase information $\phi_1$ and $\phi_2$ in the at least two raw MR data sets, as $\phi_1=\gamma B_0 TE1\alpha T$ and $\phi_2=\gamma B_0 TE2\alpha T$ and averaging the respectively weighted phase information $\phi_1$ and $\phi_2$ contained in the at least two raw MR data sets; and
    from said processor, displaying an image of the examination subject formed from said magnitude image data set and said phase image data set, with said temperature T being represented in the displayed image by the phase information in the phase image data set obtained by said weighting and said averaging.

2. Method according to claim 1, further comprising generating the phase image data set, by averaging the phase information contained in the at least two raw MR data sets ensues depending on a variance of the phase information respectively contained in the at least two raw MR data sets.

3. Method according to claim 1, further comprising detecting gradient echoes as said echo signals.

4. A method according to claim 1, further comprising, in said processor, generating said phase image data set by generating an intermediate phase image data set from said first raw MR data set and generating a second intermediate phase image data set from said second raw MR image data set, and generating a phase different data set by subtracting said first intermediate phase image data and said second intermediate phase image data set from each other and determining said temperature T as a temperature difference $\Delta T$ from a phase difference $\Delta\phi$ in said phase difference data set, said temperature difference $\Delta T$ representing a temperature change that occurred between respective acquisitions of said first and second echo signals.

5. Method according to claim 4, further comprising operating said MR data acquisition unit to acquire a plurality, that is more than two, of echo signals from the excited nuclei and, in said processor, generating a plurality of raw MR data sets respectively from the plurality of echo signals, each of said raw MR data sets being comprised of pixels, and calculating $\Delta T$ as a temperature change $\Delta Tij$ in a pixel i,j as $$\Delta T_{ij} = \frac{1}{\sum_{n=1}^{N} TE_n}\left(\sum_{n=1}^{N} TE_n \Delta T_{ij}^n\right) = \frac{k}{\sum_{n=1}^{N} TE_n}\left(\sum_{n=1}^{N} \Delta\varphi_{ij}^n\right)$$

wherein $\Delta Tij$ is a temperature difference determined in the pixel i,j, $TE_n$ are the different echo times at which echo signals have been acquired, with n =1 through N and N being a number of echoes acquired in total, k is a constant, $\Delta T_{ij}^n$ is a temperature difference calculated for the n-th echo in the pixel i,j, and $\phi_{ij}^n$ is an associated phase difference.

6. Method according to claim 5, further comprising determining a value range of the phase information at the first echo time TE1 from phase information in the phase difference data set that was generated at the first echo time TE1, and determining additional value ranges of the phase information at echo times that are longer. than TE1 based on the value range at the first echo time TE1, and determining whether the additional value ranges exceed the $2\pi$ and how often the additional value changes exceed $2\pi$.

7. A magnetic resonance MR system, comprising:
    an MR data acquisition unit;
    a controller configured to operate the MR data acquisition unit according to an MR data acquisition pulse sequence, while the examination subject is situated in a basic magnetic field $B_0$ in the data acquisition unit, wherein nuclei in the examination subject are excited at a resonance frequency and first echo signals from the excited nuclei are detected after a first echo time TE1 in said sequence and second echo signals from the excited nuclei are detected after a second echo time TE2 in said sequence that is longer than TE1;
    said controller being further configured to generate a first raw MR data set in which said first echo signals are represented and to generate at least one second raw MR data set in which said second echo signals are represented, thereby producing at least two raw MR data sets, each of said at least two raw MR data sets comprising magnitude information and phase information $\phi$, and said phase information $\phi$ in each of said at least two raw MR data sets having a relation to temperature T of the examination subject that is dependent on the respective echo time during which the respective echo signals were acquired that are represented in the at least two raw MR data sets, according to $\phi=\gamma B_0 TE\alpha T$, wherein $\phi$ is $\phi_1$ or $\phi_2$, $\gamma$ is the gyromagnetic ration for said nuclei, TE is TE1 or TE2, and $\alpha$ is the dependency of T on the resonance frequency of the nuclei;
    a computerized processor configured to generate a magnitude image data set from the at least two raw MR data sets by averaging the magnitude information in the at least two raw MR data sets;

said processor being further configured to generate a phase image data set from the phase information φ contained in the at least two raw MR data sets, by weighting respective phase information $\phi_1$ and $\phi_2$ in the at least two raw MR data sets, as $\phi_1=\gamma B_0 TE1\alpha T$ and $\phi_2=\gamma B_0 TE2\alpha T$ and by averaging the respectively weighted phase information $\phi_1$ and $\phi_2$ contained in the at least two raw MR data sets;

a display in communication with said processor; and said processor being configured to cause an image of the examination subject to be displayed at said display unit, said image being formed from said magnitude image data set and said phase image data set, with said a temperature T being represented in the displayed image by the phase information in the phase image data set obtained by said weighting and said averaging.

8. A non-transitory computer-readable storage medium encoded with programming instructions, said programming instructions causing a computerized processor system, in which said storage medium is loaded, to display a representation of a temperature in a magnetic resonance (MR) magnitude image of an examination subject, by causing said computerized processor system to:

operate an MR data acquisition unit according to an MR data acquisition pulse sequence, while the examination subject is situated in a basic magnetic field $B_0$ in the data acquisition unit, and wherein nuclei in the examination subject are excited at a resonance frequency to detect first echo signals from the excited nuclei after a first echo time TE1 in said sequence and to detect second echo signals from the excited nuclei after a second echo time TE2 in said sequence that is longer than TE1;

generate a first raw MR data set in which said first echo signals are represented and generating at least one second raw MR data set in which said second echo signals are represented, thereby producing at least two raw MR data sets, each of said at least two raw MR data sets comprising magnitude information, and phase information φ, and said phase information φ in each of said at least two raw MR data sets having a relation to temperature T of the examination subject that is dependent on the respective echo time during which the respective echo signals were acquired that are represented in the at least two raw MR data sets, according to $\phi=\gamma B_0 TE\alpha T$, wherein φ is $\phi_1$ or $\phi_2$, y is the gyromagnetic ration for said nuclei, TE is TE1 or TE2, and α is the dependency of T on the resonance frequency of the nuclei;

generate a magnitude image data set from the at least two raw MR data sets by averaging the magnitude information in the at least two raw MR data sets;

generate a phase image data set from the phase information φ contained in the at least two raw MR data sets, by weighting respective phase information $\phi_1$ and $\phi_2$ in the at least two raw MR data sets as $\phi_1=\gamma B_0 TE1\alpha T$ and $\phi_2=\gamma B_0 TE2\alpha T$, and by averaging the respectively weighted phase information contained in the at least two raw MR data sets; and display an image of the examination subject formed from said magnitude image data set and said phase image data set, with said temperature T being represented in the displayed image by the phase information in the phase image data set obtained by said weighting and said averaging.

* * * * *